United States Patent
Song et al.

(10) Patent No.: US 6,528,290 B1
(45) Date of Patent: Mar. 4, 2003

(54) CANDIDA MAGNOLIAE PRODUCING MANNITOL AND FERMENTATION METHOD FOR PRODUCING MANNITOL

(75) Inventors: Kyung Hwa Song, Kyunggi-Do (KR); Hong Baek, Junranam-Do (KR); Song Mi Park, Choongchungnam-Do (KR); Hyung Hwan Hyun, Kyunggi-Do (KR); Soo Ryun Jung, Seoul (KR); Sang Yong Kim, Kyunggi-Do (KR); Jung Kul Lee, Kyunggi-Do (KR); Ji Yoon Song, Seoul (KR)

(73) Assignees: BioNgene Co., Ltd., Seoul (KR); Bolak Co., Ltd., Kyunggi-Do (KR)

( * ) Notice: Subject to any disclaimer, the term of this patent is extended or adjusted under 35 U.S.C. 154(b) by 0 days.

(21) Appl. No.: 09/978,559

(22) Filed: Oct. 18, 2001

(30) Foreign Application Priority Data

Apr. 4, 2001 (KR) .............................. 01-17904

(51) Int. Cl.⁷ .............................. C12P 7/18; C12N 1/16
(52) U.S. Cl. .................. 435/158; 435/254.22; 435/921
(58) Field of Search .................. 435/155, 158

(56) References Cited

PUBLICATIONS

J. Chem. Tech. Biotechnol., 1988, pp. 223–228: H.V. Hendriksen et al.: *Production of Mannitol by Penicillium Strains*.

Biotechnology and Bioengineering, vol. XII, pp. 913–920, 1970, Hiroshi Onishi et al.: *Microbial production of D–Mannitol and D–Fructose from Glycerol*.

Journal of Fermentation and Bioengineering, vol. 85, No. 2, pp. 203–208, 1998, Jong Won Yun et al.: *A Comparative Study of Mannitol production by Two Lactic Acid Bacteria*.

Can. J. Microbiol., vol. 22, pp. 808–816, 1976, Vichai Boonsaeng et al.: *Mannitol Production in Fungi During Glucose Catabolism*.

*Primary Examiner*—Herbert J. Lilling
(74) *Attorney, Agent, or Firm*—Kenyon & Kenyon

(57) ABSTRACT

The present Invention is to provide a novel strain, *Candida magnoliae* (KCCM-10252) producing mannitol isolated from the fermentation sludge collected from a xylitol manufacturing company, and further a method for manufacturing mannitol with high yield and high productivity by optimizing various culture conditions and medium composition using the new strain, *Candida magnoliae*.

2 Claims, No Drawings

CANDIDA MAGNOLIAE PRODUCING MANNITOL AND FERMENTATION METHOD FOR PRODUCING MANNITOL

BACKGROUND OF THE INVENTION

The present invention relates to a fermentation process for producing mannitol from fructose using a novel strain, *Candida magnoliae* (KCCM-10252) producing mannitol in high yield and high productivity, and a novel strain of *Candida magnoliae* (KCCM-10252) which is isolated from a natural substance.

Mannitol is a six carbon sugar alcohol, and it is contained in natural substances, such as, brown algae, mushrooms, fungi and the like in nature. Since it has 30~40% of sugar's sweetness, not only it can be used as an alternative sweetening agent in the food processing industry where the use of sugar is limited, but also it can be mostly used as an additive for confectionary, a filler for medicine, a surfactant, a waterproof agent and the like, because it has superior properties, such as, a cool taste, low hygroscopic property, fluidity and the like. Further, it has been widely used in the food and pharmaceutical industry, for example, as a therapeutic intermediate of hypotension and a coating agent for reducing a bitter taste during the manufacturing various drugs.

Mannitol exists in many kinds of fruits or vegetables as a natural product in a very small amount. Therefore, it is industrially of little economical value to extract mannitol from fruits or vegetables.

One of the commercialized methods for producing mannitol comprises i) isolating the fructose formed by hydrolysis from sugar and the like ; and ii) manufacturing the mannitol by hydrogenation to the fructose in the presence of a catalyst under high temperature and high pressure. However, since the sorbitol is produced as a by-product in such manufacturing process, it is required to purify the mannitol in order to eliminate the sorbitol as a separate step. Of course, the conversion yield is so much low that its production cost becomes high. Further, such manufacturing process has handicaps, such as, a risk of dangerousness and requirement of wastes treatment, because it includes the reaction under high temperature and high pressure.

In order to solve such drawbacks, many studies on a method for producing mannitol by using microorganisms have been conducted. As the known microorganisms related with production of mannitol, in case of any yeast, there are *Candida zeylannoide, Candida lipolitica, Cryptococcus neoformans, Torulopsis mannitofaciens*, etc.,; in case of bacteria, there are *Lactobacillus brevis, Leuconostoc mesenteriode, Mycobacterium smegmatis*, etc.,; and in case of fungi, there are *Mucor rouxii, Aspergillus nidulans, Penicillum scabrosum*, etc. The method for producing mannitol by using microorganisms has a high economical value. Further, since only mannitol can be specifically produced from glucose or fructose according to the method, the process for isolating and purifying mannitol after completion of the fermentation for mannitol can be performed with much convenience. However, it is difficult to industrialize this method, because its productivity and yield is not so high.

SUMMARY OF THE INVENTION

It is, therefore, an objective of the present invention to provide a method for producing mannitol in high productivity and high yield by isolating, identifying and developing a new strain, *Candida magnoliae* producing mannitol in high yield from a fermentation sludge collected from xylitol manufacturing company (Bolak Co., Ltd., Osan, Korea) and further optimizing culture conditions.

The object of the present invention is to provide novel strain of *Candida magnoliae*, which was deposited Korea Culture Center of Microorganism, 361–221, Yurim B/D Hongje-1-dong, Seodaemun-gu, Seoul, 120–091, Republic of Korea with accession number KCCM-10252 on Mar. 5, 2001 under Budapest treaty, for preparing mannitol with high yield and high productivity.

Another object of the present invention is to provide the fermentation process for manufacturing mannitol with high yield and high productivity, using strain of *Candida magnoliae* (KCCM-10252) comprising the steps of: i) fermenting glucose or fructose medium with microorganism by controlling following fermentation conditions; a) composition of medium for maximum production of mannitol consists of 50~100 g/L of glucose, 50~120 g/L of fructose, 5~20 g/L of yeast extract, 1~5 g/L of ammonium sulfate, 1.0~5.0 g/L of dibasic potassium phosphate and 0.1~0.5 g/L of magnesium sulfate; b) pH of culture medium is 4.5~5.5; c) temperature of cultivation is 27~35° C.; d) aeration rate is 0~0.5 volume of air per volume of medium per minute; and e) agitation speed of the medium is 200~500 rpm; ii ) removing the cells and other residue from the fermentation medium; and iii) separating and recovering mannitol from the fermentation medium of step ii).

The further object of the present invention is to provide a fermentation process wherein the strain used for fermentation is prepared by cultivating frozen *Candida magnoliae* (KCCM-10252) in YPD medium comprising 15~25 g/L of glucose, 7~13 g/L of yeast extract and 15~25 g/L of peptone.

Also, the present Invention is to provide an isolating method for novel strain, *Candida magnoliae* (KCCM-10252), comprising steps of i) sorting a single colony growing fast at 27~33° C. by using a plate containing 10~20 g/L of glucose, 18~22 g/L of fructose, 15~25 g/L of peptone, 7~15 g/L of yeast extract and 12~17 g/L of agar after diluting a natural sludge sample; ii) sorting the strain producing mannitol most after fermenting such sorted strains in the medium containing 30~70 g/L of glucose, 50~100 g/L of fructose, 5~20 g/L of yeast extract, 1~5 g/L of ammonium sulfate and 1~5 g/L of dibasic potassium phosphate for 68~76 hours, and iii) isolating the novel strain, *Candida magnoliae* (KCCM-10252) producing the mannitol.

DETAILED DESCRIPTION OF THE INVENTION

The method for isolating the new strain, *Candida magnoliae* according to the present Invention is described as follows.

After properly diluting a fermentation sludge sample collected from xylitol manufacturing company, a single colony with priority given to strains growing fast at 27~33° C. was sorted by using the plate containing 200~400 g/L of glucose, 15~25 g/L of peptones, 7~15 g/L of yeast extract and 12~17 g/L of agar, and further the strain producing mannitol most was finally sorted after such sorted strains were fermented in the medium containing 30~70 g/L of glucose, 50~100 g/L of fructose, 5~20 g/L of yeast extract, 1~5 g/L of ammonium sulfate and 1~5 g/L of dibasic potassium phosphate for 68~76 hours.

For identification of the strain, the method (Kurtzman & Robnett, 1998) for analyzing the nucleotide sequence of 26s rRNA and the morphological, cultural, and physiological properties thereof were examined in accordance with Yarrow's method (Elsevier Science Publishers, Amsterdam, 1998) and further the strain was identified according to the classification method of Barnett, et al.(Yeasts: Characteristics and identification. Cambridge University Press, London, 1983). The results of analyzing the nucleotide sequence of 26s rRNA of the sorted strain and the nucleotide sequence of similar seeds are shown in Table 1 and Table 2, respectively.

TABLE 1

Nucleotide Sequence of 26s rRNA of the New Strain,
Candida magnoliae producing Mannitol

```
5'-AACTTAAGCATATCAATAAGCGGAGGAAAAGAAACCAACAGGGATTGCCC
TAGTAATGGCGAATGAACAGGCAAAAGCTCAGATTTGAAACCCTCGGGAT
TGTAATCTGGAGACCTGGATTTGGCACGCTGACCAAGTCTTCTGGAACGG
AGCGCCATGGAGGGTGACAGCCCCGTAGCAGCAGCCGCAGTAAATCCGGG
TCGACGAGTCGAGTTGTTTGGGAATGCAGCTCTAAGTGGGTGGTATGCTC
CATCTAAAGCTAAATATTGGCGAGAGACCGATAGCGAACAAGTACTGTGA
AGGAAAGATGAAAAGAACTTTGAAAAGAGAGTGAAAAAGTACGTGAAATT
GTTGAAATGGAAGGCAATGAGGTGCGATTGACCCGGACGTTTGCGGGCAG
CACAAAAGCGCAGGCCGCCTCGGCATTGCCTGCGTGCATACTGCCTCGCG
GACCACCGGTTCTAACAACGCCTTATTGCAC-3'
```

TABLE 2

Similarity of Nucleotide sequence of 26s rRNA D1/D2 domain between the Novel Strain, Candida magnoliae producing Mannitol and Similar seeds

| Strain | Accession No. | Similarity (%) |
| --- | --- | --- |
| Candida magnoliae NRRL Y-2024 | U45722 | 100 |
| Candida geochares NRRL Y-17073T | U48591 | 97.56 |
| Candida vaccinii NRRL Y-17684T | U45708 | 95.77 |
| Candida apis NRRL Y-2482T | U48237 | 94.89 |
| Candida gropengiesseri NRRL Y-1445T | U45721 | 88.94 |
| Starmerela bombicola NRRL Y-17069T | U45705 | 80.9 |
| Candida etchellsii NRRL Y-17084T | U45723 | 80.32 |
| Candida bombi NRRL Y-17081T | U45706 | 80 |
| Candida floricola NRRL Y-17676T | U45710 | 80 |
| Candida stellata NRRL Y-1446T | U45730 | 79.78 |
| Candida apicola NRRL Y-2481T | U45703 | 79.28 |
| Candida lactis-condensi NRRL Y-1515T | U45724 | 78.88 |
| Candida blankii NRRL Y-17068T | U45704 | 76.8 |

Furthermore, the morphological, physiological and biochemical properties thereof are shown in Table 3. The available carbon source for the new strain is shown in Table 4.

TABLE 3

Morphological, Physiological and Biochemical Properties of the New Strain, Candida magnoliae (KCCM-10252) according to the Present Invention

| Properties | New Strain according to the Present Invention (KCCM-10252) |
| --- | --- |
| Cell Shape | Rod-coccus |
| Colony Color | White |
| Sporogenesis | – |
| Oxygen Demand | Aerobic |
| Motility | – |
| Proliferation of Bacteria by Temperatures | |
| 20° C. | + |
| 30° C. | + |
| 35° C. | + |
| 40° C. | – |
| Proliferation in a Medium from which Vitamins are removed | – |
| Urea Decomposition | – |
| Production of Acetic Acid | – |
| Formation of Starch | – |
| Formation of Diazonium Blue B | – |
| Use of Nitrate | + |

TABLE 4

Use of Carbon Source for New Strain, Candida magnoliae (KCCM-10252) according to the Present Invention

| Carbon source | Growth | Carbon source | Growth |
| --- | --- | --- | --- |
| D-glucose | + | Ribitol | – |
| Glycerol | + | Adonitol | – |
| 2-Keto-D-gluconate | – | N-Acetyl-D-glucosamine | – |
| Arabinose | – | Cellobiose | – |
| D-Xylose | – | Lactose | – |
| Sorbose | + | Maltose | – |
| Xylitol | + | Sucrose | + |
| Galactose | – | Trehalose | – |
| Inositol | – | Melezitose | – |
| Sorbitol | + | Raffinose | + |
| Mannitol | + | Starch | – |

As a result of identifying properties of the strain mentioned above, the strain proved to be of the Candida magnoliae seed. Further, the novel strain, Candida magnoliae was deposited with Korean Culture Center of Microorganisms on Mar. 5, 2001 (KCCM-10252).

The method for producing mannitol by fermentation according to the present Invention is more specifically described as follows.

The YPD medium containing 15~25 g/L of glucose, 7~13 g/L of yeast extract and 15~25 g/L of peptone was used as a growth medium for seed culture of the strain. The medium comprising 50 g/L of glucose and 100 g/L of fructose as the carbon source, yeast extract and ammonium sulfate as the nitrogen source and dibasic potassium phosphate and magnesium sulfate as inorganic salts was used as a fermentation medium of the flask. Each component's quantity may be changed in order to increase productivity of mannitol. The medium used in the fermenter was an optimum medium comprising 300 g/L (concentration of a total added quantity) of fructose, 50 g/L of glucose, 10 g/L of a yeast extract, 2.5 g/L of dibasic potassium phosphate, 2.5 g/L of ammonium sulfate and 0.4 g/L of magnesium sulfate.

The seed culture was performed by inoculating the strain kept in a cold room with 50 ml of the YPD medium contained in the 250 ml flask until the strain grew in the shaking culture medium at 230~270 rpm and 27~33° C. (for about 24 hours) so much as the concentration of the biomass thereof reached to 3~4 g/L. The flask culture was performed by inoculating the seed culture fluid equivalent to 5% of the medium with 50 ml of the fermentation medium contained in the 250 ml flask and it was cultured in the shaking culture medium at 230~270 rpm and 27~33° C. for 68~78 hours.

For the fed-batch fermenter culture, the 5L fermenter (Korea Fermenter Co., Ltd.) having 2L of the medium in which 100 g/L of fructose was contained at the initial fermentation stage was used, and the stirring rate and the ventilation volume were adjusted to 200~500 rpm and 0~0.5 vvm respectively in the fermentation process. The pH was adjusted to 4.5~5.5 in the pre-fermentation process, the culture temperature was 27~33° C., and the concentration of the maintained fructose was adjusted to 50~120 g/L.

The respective concentrations of glucose, fructose and mannitol were measured by using HPLC's Refractive Index Detector (Waters 2410, USA) having Carbohydrate Analysis Column (Waters, USA) equipped therewith. Wherein, a mixture of acetonitrile and water(8:2) was used as a solvent, and the flow rate thereof was 1.5 ml/min. For obtaining the concentration of biomass thereof, the suspension degree thereof was measured at 600 nm by using the turbidimeter and further it was converted into a dry-weight by using the standard curve as measured beforehand. The concentration of the dissolved oxygen was measured by using the dissolved oxygen electrodes of Ingold Company (Swiss, polarographic type).

EXAMPLES

The present invention is described in more details through the following examples.

Example I

Seed Culture: The strain, *Candida magnoliae* (KCCM-10252), which was isolated from a fermentation sludge collected from a xylitol manufacturing company, was inoculated with 50 ml of the YPD medium contained in the 250 ml flask and further cultured at 250 rpm and 30° C. for 24 hours.

Main Culture: After inoculating the seed culture fluid with 50 ml of the fermentation medium contained in the 250 ml flask, it was cultured in a shaking culture medium at 220 rpm and 30° C. until fructose was completely exhausted. The pH of the medium was not controlled after it was adjusted to 5.0 at the initial stage of the fermentation. Wherein, the components of the medium were 50 g/L of glucose, 100 g/L of fructose, 5 g/L of a yeast extract, 2.5 g/L of ammonium sulfate and 2.5 g/L of dibasic potassium phosphate. The results of observing production of mannitol with the passage of time are shown in table 5. The maximum specific proliferation rate of the isolated strain was 0.26 $h^{-1}$, the maximum quantity of biomass thereof was 3.9 g/L, and 42 g/L of mannitol was produced.

TABLE 5

Production of Mannitol by the Isolated Strain with the Passage of Time in the 250 ml Flask

| Culture time (hr) | Cell mass (g/L) | Mannitol (g/L) |
| --- | --- | --- |
| 0 | 0.07 | |
| 12 | 0.78 | |
| 18 | 2.91 | 0.8 |
| 36 | 3.72 | 9.1 |
| 48 | 3.84 | 21.3 |
| 60 | 3.91 | 33.6 |
| 72 | 3.93 | 42.2 |

Example II

The culturing method was the same as that described in Example 1, except that the fermentation culture was carried out for 72 hours in the fermentation medium comprising respective nitrogen sources equivalent to respective nitrogen content of 50 g/L of glucose, 100 g/L of fructose, 2.5 g/L of ammonium sulfate, 2.5 g/L of dibasic potassium phosphate and 5 g/L of a yeast extract. After such culture, respective effects of various nitrogen sources on production of mannitol was looked into. The results of culturing the strain in various nitrogen source are shown in Table 6. Mannitol was found to be of a low concentration in other organic nitrogen sources than the yeast extract and the yeast nitrogen base. And, the yeast extract was the best nitrogen source.

TABLE 6

Effect of Nitrogen Source on Production of Mannitol in the 250 ml flask

| N source | Cell mass (g/L) | Mannitol (g/L) |
| --- | --- | --- |
| Yease extract | 3.93 | 42.2 |
| Yease nitrogen base | 4.20 | 32.2 |
| Tryptone | 2.62 | 15.3 |
| Soybean | 3.86 | 6.8 |
| Corn steep liquor | 1.25 | 3.6 |
| Malt extract | 2.41 | 3.5 |
| Peptone | 2.24 | 2.8 |

Example III

The culturing method was the same as that described in Example 1, except that the main culture was carried out for 72 hours in the fermentation medium containing 50 g/L of glucose, 100 g/L of fructose, 2.5 g/L of ammonium sulfate, yeast extract and 2.5 g/L of dibasic potassium phosphate by changing the concentration of the yeast extract among them. The results of culturing so are shown in Table 7

TABLE 7

Quantity of Mannitol produced in the 250 ml flask by Concentrations of the Yeast Extract

| Yeast extract (g/L) | Cell mass (g/L) | Mannitol (g/L) |
| --- | --- | --- |
| 0 | 0.0 | 0.0 |
| 1 | 0.7 | 0.0 |
| 2 | 2.2 | 8.8 |
| 5 | 3.9 | 42.2 |
| 7 | 4.1 | 45.6 |
| 10 | 4.0 | 48.5 |
| 15 | 3.4 | 43.1 |
| 20 | 2.3 | 34.4 |

Example IV

The culturing method was the same as that described in Example 1, except that the main culture was carried out for 72 hours in the fermentation medium containing 50 g/L of glucose, 100 g/L of fructose, 10 g/L of yeast extract, 2.5 g/L ammonium sulfate and dibasic potassium phosphate by changing the concentration of dibasic potassium phosphate among them. The result of culturing so are shown in Table 8.

TABLE 8

Quantity of Mannitol produced in the 250 ml flask by Concentrations of Potassium phosphate

| Magnesium sulfate (g/L) | Cell mass (g/L) | Mannitol (g/L) |
| --- | --- | --- |
| 0.0 | 4.0 | 48.6 |
| 0.1 | 4.0 | 49.5 |
| 0.2 | 4.1 | 50.3 |
| 0.4 | 4.1 | 52.0 |
| 0.6 | 4.0 | 48.2 |
| 0.8 | 3.8 | 44.8 |

Example V

The culturing method was the same as that described in Example 1, except that the main culture was carried out for 30 hours in the fermentation medium containing 100 g/L of fructose, 10 g/L of yeast extract, 2.5 g/L of dibasic potassium phosphate, 2.5 g/L of ammonium sulfate and magnesium sulfate by changing the concentration of magnesium sulfate among them. The result of culturing so are shown in Table 9

TABLE 9

Quantity of Mannitol produced in the 250 ml flask by Concentrations of Magnesium Sulfate

| Potassium phosphate (g/L) | Cell mass (g/L) | Mannitol (g/L) |
|---|---|---|
| 0 | 0.0 | 0.0 |
| 1 | 3.6 | 45.2 |
| 2.5 | 4.0 | 48.8 |
| 5 | 3.9 | 46.0 |
| 10 | 3.4 | 40.9 |

Example VI

The culturing method was the same as that described in Example 1, except that the main culture was carried out in the 5L fermenter having 3L of an optimum fermentation medium (containing 50 g/L of glucose, 100 g/L of fructose, 10 g/L of yeast extract, 2.5 g/L of ammonium sulfate, 2.5 g/L of dibasic potassium phosphate and 0.4 g/L of magnesium sulfate). The experiment was conducted at the culture temperature of 30° C. by pH's thereof. The results of culturing with the ventilation volume and the stirring rate being adjusted to 0.5 vvm and 200~500 rpm respectively by changing the pH thereof until fructose was completely exhausted are shown in Table 10.

TABLE 10

Quantity of Mannitol produced in the 5 L fermenter by pH's

| pH | Cell mass (g/L) | Mannitol (g/L) | Culture time (h) |
|---|---|---|---|
| 4.0 | 9.2 | 62.8 | 60 |
| 4.5 | 11.3 | 74.1 | 60 |
| 5.0 | 12.0 | 78.0 | 60 |
| 5.5 | 12.4 | 75.2 | 60 |
| 6.0 | 12.2 | 68.7 | 60 |

Example VII

The culturing method and the fermentation medium were the same as those described in Example 6, except that the main culture experiment was carried out at the culture pH of 5.0 by culture temperatures. The results of such experiment are shown in Table 11.

TABLE 11

Quantity of Mannitol produced in the 5 L fermenter by Culture Temperatures

| Temperature (° C.) | Cell mass (g/L) | Mannitol (g/L) | Culture time (h) |
|---|---|---|---|
| 25 | 7.8 | 66.5 | 120 |
| 27 | 11.9 | 75.7 | 92 |
| 30 | 12.0 | 78.2 | 60 |
| 33 | 10.5 | 75.3 | 72 |
| 35 | 8.2 | 74.0 | 80 |

Example VIII

A fed-batch culture was carried out in the selected optimum medium (10 g/L of yeast extract, 2.5 g/L of dibasic potassium phosphate, 0.4 g/L of magnesium sulfate) contained in the fermenter by increasing the concentration of fructose to 300 g/L. Wherein, the reason why the fed-batch culture was performed was because the production rate of mannitol was decreased in 100 g/L of fructose or more in case of *Candida magnoliae*. Such culture was performed by using the 5L fermenter(Korea Fermenter Co., Ltd.) having 2L of medium containing 50 g/L of glucose as a carbon source at the initial fermentation stage. The fed-batch culture of which the final culture fluid got to be 3L (the concentration of the total added fructose was equivalent to 300 g/L) was performed by adding 250 ml of solution containing 225 g of fructose four times (20 h, 36 h, 62 h, 90 h) in the fermentation process. Dissolved oxygen was kept at 20% or more at the initial culture stage by adjusting the stirring rate to 500~600 rpm, and then it was limited by changing the stirring rate to 200~250 rpm at the time when the concentration of biomass thereof got to be about 5 g/L. The pH thereof was adjusted to 5.0, the culture temperature was adjusted to 30° C., and the ventilation volume was adjusted to 5.0 vvm for the entire fermentation process. Production of mannitol with the passage of time is shown in Table 12, As a result of performing such fed-batch culture as above, 248 g/L of mannitol was obtained from 300 g/L of fructose in 120 hours. This result is equivalent to it that the yield of mannitol from fructose is 83% and the productivity of mannitol is 2.07 g/L-h.

TABLE 12

Quantity of Mannitol produced from 300 g/L of Fructose in the 5 L fermenter by Hours

| Fermentation time (h) | Cell mass (g/L) | Mannitol (g/L) |
|---|---|---|
| 0 | 0.1 | 0 |
| 12 | 6.4 | 0 |
| 24 | 10.4 | 8.0 |
| 36 | 12.8 | 24.3 |
| 48 | 12.2 | 46.4 |
| 60 | 11.0 | 100.1 |
| 72 | 10.4 | 152.7 |
| 84 | 9.8 | 199.2 |
| 96 | 9.6 | 214.6 |
| 108 | 9.0 | 226.6 |
| 120 | 8.5 | 248.0 |

The present Invention enables mannitol to be produced in high yield and high productivity by culturing the new strain, *Candida magnoliae* isolated from a natural sludge in a medium containing 50~100 g/L of glucose, 50~20 g/L of fructose, 5~20 g/L of yeast extract, 1.0~5.0 g/L of potassium phosphate dibasic and 0.1~0.5 g/L of magnesium sulfate. Particularly, the present Invention enables mannitol to be produced through fermentation more selectively, economically and effectively than the prior chemical synthetic and fermentation method, and therefore, it can provide an advantage to any mannitol manufacturer in the product quality and the international competitiveness over other manufacturers using the prior art.

What is claimed is:

1. A fermentation process for manufacturing mannitol with high yield and high productivity, using strain of *Candida magnoliae* (KCCM-10252) comprising the steps of:

i) fermenting glucose or fructose medium with microorganism by controlling following fermentation conditions;

a) composition of medium for maximum production of mannitol consists of 50~100 g/L of glucose, 50~120 g/L of fructose, 5~20 g/L of yeast extract 1~5 g/L of ammonium sulfate, 1.0~5.0 g/L of dibasic potassium phosphate and 0.1~0.5 g/L of magnesium sulfate;
b) pH of culture medium is 4.5~5.5;
c) temperature of cultivation is 27~35° C.;
d) aeration rate is 0~0.5 volume of air per volume of medium per minute; and
e) agitation speed of the medium is 200~500 rpm;

ii) removing the cells and other residue from the fermentation medium; and iii) separating and recovering mannitol from the fermentation medium of step ii).

2. The fermentation process for manufacturing mannitol according to claim 1, wherein the strain used for fermentation is prepared by cultivating frozen *Candida magnoliae* (KCCM-10252) in YPD medium comprising 15~25 g/L of glucose, 7~13 g/L of yeast extract and 15~25 g/L of peptone.

* * * * *

SEQUENCE LISTING

<160> NUMBER OF SEQ ID NOS: 1

<210> SEQ ID NO 1
<211> LENGTH: 480
<212> TYPE: DNA
<213> ORGANISM: Candida magnoliae

<400> SEQUENCE: 1

```
aacttaagca tatcaataag cggaggaaaa gaaaccaaca gggattgccc tagtaatggc      60
gaatgaacag gcaaaagctc agatttgaaa ccctcgggat tgtaatctgg agacctggat     120
tggcacgctg accaagtctt ctggaacgga gcgccatgga gggtgacagc cccgtagcag     180
cagccgcagt aaatccgggt cgacgagtcg agttgtttgg gaatgcagct ctaagtgggt     240
ggtatgctcc atctaaagct aaatattggc gagagaccga tagcgaacaa gtactgtgaa     300
ggaaagatga aagaactttt gaaaagagag tgaaaaagta cgtgaaattg ttgaaatgga     360
aggcaatgag gtgcgattga cccggacgtt tgcgggcagc acaaaagcgc aggccgcctc     420
ggcattgcct gcgtgcatac tgcctcgcgg accaccggtt ctaacaacgc cttattgcac     480
```